US00PP27056P2

(12) United States Plant Patent
Nishikawa

(10) Patent No.: US PP27,056 P2
(45) Date of Patent: Aug. 9, 2016

(54) ***DELOSPERMA* PLANT NAMED 'DSAB13-1'**

(50) Latin Name: *Delosperma cooperi*
Varietal Denomination: DSAB13-1

(71) Applicant: Koichiro Nishikawa, Katuta-gun (JP)

(72) Inventor: Koichiro Nishikawa, Katuta-gun (JP)

( * ) Notice: Subject to any disclaimer, the term of this patent is extended or adjusted under 35 U.S.C. 154(b) by 92 days.

(21) Appl. No.: 14/544,006

(22) Filed: Nov. 13, 2014

(51) Int. Cl.
*A01H 5/02* (2006.01)

(52) U.S. Cl.
USPC ..... Plt./422

(58) Field of Classification Search
USPC ..... Plt./422
See application file for complete search history.

*Primary Examiner* — Susan McCormick Ewoldt
(74) *Attorney, Agent, or Firm* — Penny J. Aguirre

(57) ABSTRACT

A new cultivar of *Delosperma* plant, 'DSAB13-1', that is characterized by its compact and very horizontal plant habit, its relatively small leaves, its very floriferous and long blooming flowering habit, and its flowers with petals that are bright red-purple in color, petaloids that are white with light purple tips and anthers that are yellow.

2 Drawing Sheets

Botanical classification: *Delosperma cooperi.*
Variety denomination: 'DSAB13-1'.

CROSS REFERENCE TO RELATED APPLICATIONS

This application is co-pending with U.S. Plant Patent Applications filed for plants derived from the same breeding program that are entitled Delosperma Plant Named 'DSAA13-1' (U.S. Plant patent application Ser. No. 14/544,004), *Delosperma* Plant Named 'DSAM13-1' (U.S. Plant patent application Ser. No. 14/544,007).*

BACKGROUND OF THE INVENTION

The present invention relates to a new and distinct cultivar of *Delosperma* plant, botanically known as *Delosperma cooperi* 'DSAB13-1' and will be referred to hereinafter by its cultivar name, 'DSAB13-1'. The new cultivar of *Delosperma* is a herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'DSAB13-1' was selected in the Inventor's trial garden in 2012 as a single unique plant from amongst the seedlings derived from self-crossing an unnamed and unpatented plant from the Inventor's breeding program in 2011. The Inventor's reference number for the parent plant is DSARW12-2.

Asexual propagation of the new cultivar was first accomplished by softwood cuttings in 2012 by the Inventor in Ichinimiya-City, Aichi-Pref, Japan. Asexual propagation by softwood cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'DSAB13-1' as a unique cultivar of *Delosperma.*

1. 'DSAB13-1' exhibits a compact and very horizontal plant habit.
2. 'DSAB13-1' exhibits relatively small leaves.
3. 'DSAB13-1' exhibits a very floriferous and long blooming flowering habit.
4. 'DSAB13-1' exhibits flowers with petals that are bright red-purple in color, petaloids that are white with light purple tips and anthers that are yellow.

The parent plant of 'DSAB13-1', Ref. No. DSARW12-2, differs from 'DSAB13-1' in having flowers with petals that are lighter purple-pink in color. 'DSAB13-1' can also be most closely compared to cultivars with co-pending patent applications from the same breeding program that differ from 'DSAB13-1' mostly in flower color; 'DSAA13-1' and 'DSAM13-1'. 'DSAA13-1' differs from 'DSAB13-1' in having flowers with petals that are red-orange in color at the apex blending into red-purple near the base. 'DSAM13-1' differs from 'DSAB13-1' in having flowers with petals that are bright red purple in color at the apex and lighter red-purple near the base.

BRIEF DESCRIPTION OF THE DRAWINGS

The accompanying colored photographs illustrate the overall appearance and distinct characteristics of the new *Delosperma*. The plant in the photograph is 2 months in age as grown in a 12-cm container outdoors in Lisse, The Netherlands.

The photograph in FIG. 1 provides a side view of 'DSAB13-1' in bloom.

Figure 1:
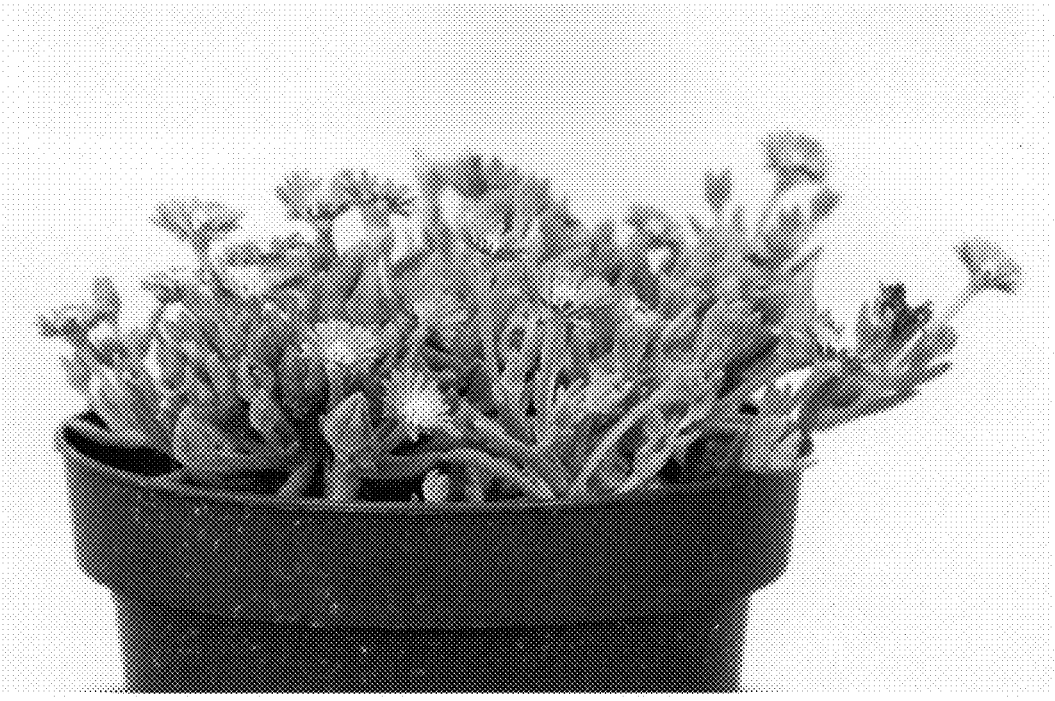
Figure 2:
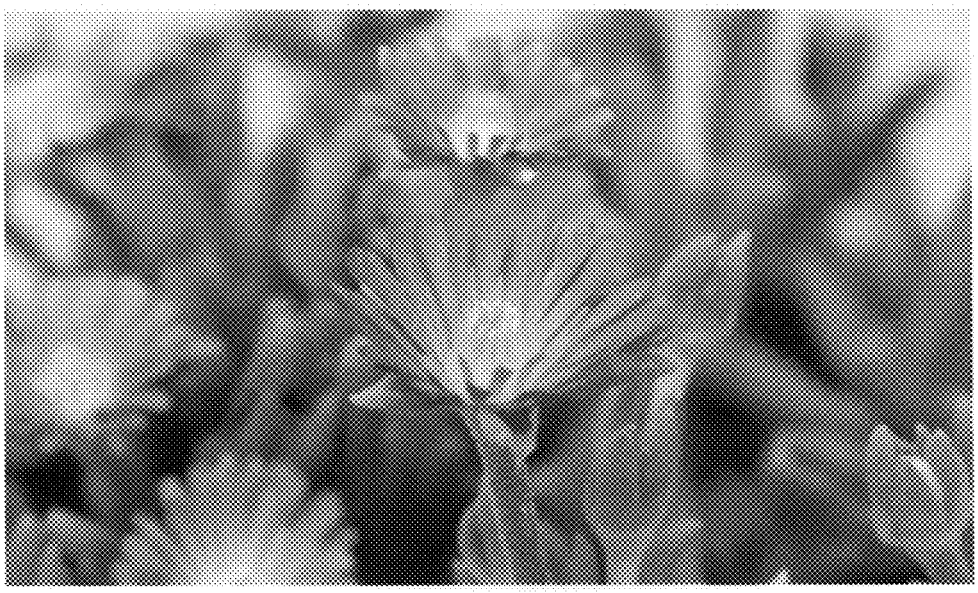

The photograph in FIG. 2 provides a close-up view of a flower of 'DSAB13-1'.

Figure 3:
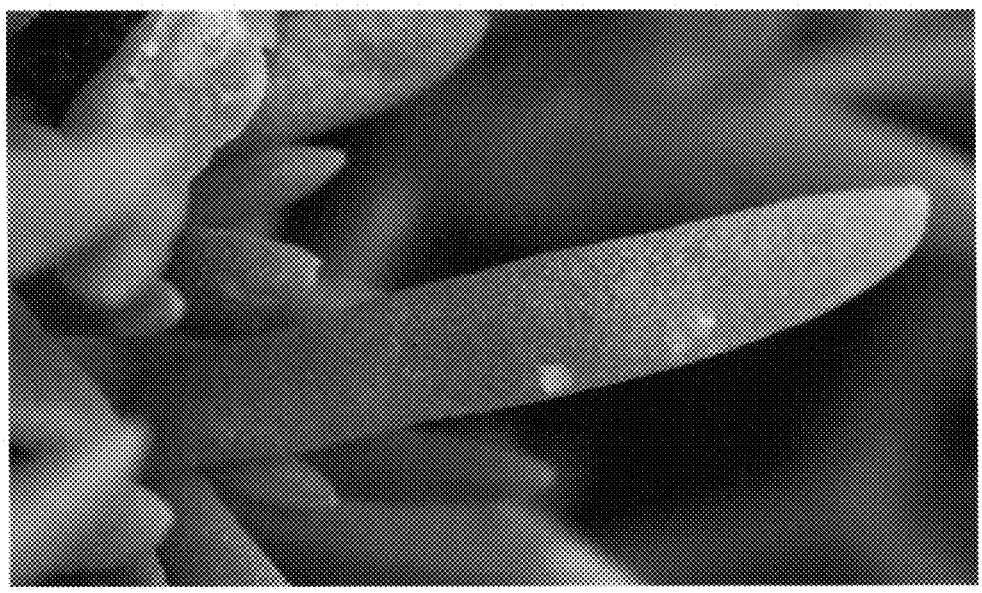

The photograph in FIG. 3 provides a close-up view of the foliage of 'DSAB13-1'.

The colors in the photographs may differ slightly from the color values cited in the detailed botanical description, which accurately describe the colors of the new *Delosperma.*

DETAILED BOTANICAL DESCRIPTION

The following is a detailed description of two month-old plants of the new cultivar as grown in 12-cm containers outdoors in Lisse, The Netherlands. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period*.—Mid April to mid September in Noordwijkerhout, The Netherlands.

*Plant type*.—Herbaceous perennial.

*Plant habit*.—Compact and very horizontal.

*Plant size*.—About 5.3 cm in height and about 13.6 cm in diameter as grown in a 12-cm container.

*Cold hardiness*.—Observed to be hardy to U.S.D.A. Zone 7.

*Diseases*.—No more susceptible or resistant to diseases than other *Delosperma cooperi* varieties.

*Root description*.—Fibrous roots.

*Propagation*.—Softwood cuttings.

*Growth habit*.—Vigorous.

*Root development*.—Roots initiate and fill a 104-cell plug in 3 weeks and the planted plugs fully develop in 9-cm container within 6 weeks.

Stem description:

*Shape*.—Round.

*Stem color*.—147D, upper side strongly tinged 174A to 174B.

*Stem size*.—Lateral branches; an average of 4.6 cm in length and 2 mm in diameter.

*Internode length*.—An average of 1.7 cm.

*Stem substance*.—Succulent.

*Stem surface*.—Moderately glossy, densely pubescent with very short glandular hairs; an average of 0.2 mm in length and 156D in color.

*Branching habit*.—Average of 20 lateral branches.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, slightly pubescent with very short glandular hairs; to small to measure size, 157D in color.

*Leaf color*.—Young upper and lower surface; 137D, mature upper and lower surface; 138A

*Leaf size*.—About 2.6 cm in length and 3.5 mm in width.

*Leaf quantity*.—Average of 6 (3 pairs) per lateral branch.

*Leaf attachment*.—Sessile.

Inflorescence description:

*Inflorescence type*.—Flowers solitary.

*Flower number*.—An average of 2 per lateral stem, 160 flowers and buds per plant in a 12-cm container.

*Flower fragrance*.—Faint, sweet and pleasant.

*Flower aspect*.—Upright to slightly outward.

*Flower longevity*.—A few days.

*Flower type*.—Single.

*Flower size*.—Average of 1.6 cm in diameter and 7 mm in depth.

*Flower buds*.—Broadly ovate, an average of 7 mm in length and 4 mm in diameter, color; 138B, tinged 180D, base 144C.

*Calyx*.—Rotate in shape, average of 5 mm in depth and 1.3 cm in diameter.

*Sepals*.—5, broad ovate in shape, margin entire, an average of 5 mm in length and 3 mm in width, broadly acute apex, broadly cuneate base, both surfaces finely pubescent, color young and mature upper and lower surface; 138B.

*Petals*.—An average of 44 per flower, rotate and slightly curved, narrowly oblanceolate in shape, surface is smooth and glossy on both surfaces, margin entire, apex obtuse, base cuneate, an average of 6 mm in length and 1 mm in width, color: opening flowers upper and lower surfaces; between 72A and N74A, fully opened flowers upper and lower surface; N74A.

*Petaloids*.—An average of 30 per flower, rotate and near vertical surrounding stamens, lanceolate in shape, surface is moderately to highly glossy on both surfaces, margin entire, apex acute, base truncate, an average of 3 mm in length and 0.5 mm in width, color of immature and mature upper and lower surface NN155C, tip is 75A.

*Peduncle*.—Average of 1.8 cm in length and 1.5 mm in diameter, weak in strength, straight on top of lateral branch at 0°, 179C to 179D in color, surface moderately glossy, sparsely to moderately pubescent with very short glandular hairs.

*Pedicel*.—None, individual flowers directly on pedicels.

Reproductive organs:

*Pistils*.—5, an average of 1.8 mm in length, style and stigma are not distinguishable, 144B to 144C in color, ovary is 143C in color.

*Stamens*.—Average 60, anthers are dorsifixed, narrowly oblong in shape, an average of 0.5 mm in diameter, filaments are 1.5 mm in length and NN155D in color, stamen is 13A in color, pollen is moderate to high in quantity and 13C in color.

*Fruit*.—Fruit and seed production was not observed under the conditions tested.

It is claimed:

1. A new and distinct variety of *Delosperma* plant named 'DSAB13-1' as described and illustrated herein.

* * * * *